United States Patent [19]
de Labbey et al.

[11] Patent Number: 5,932,201
[45] Date of Patent: Aug. 3, 1999

[54] REDUCING COMPOSITION COMPRISING A BASIC AMINO ACID AND A CATIONIC POLYMER

[75] Inventors: Arnaud de Labbey, Aulnay-sous-Bois; François Pataut, Paris, both of France

[73] Assignee: L'Oreal, Paris, France

[21] Appl. No.: 08/591,910

[22] Filed: Jan. 25, 1996

[30] Foreign Application Priority Data

Jan. 30, 1995 [FR] France .................................. 95 01038

[51] Int. Cl.$^6$ .............................. A61K 7/09; A61K 7/11
[52] U.S. Cl. ........................................ 424/70.17; 206/568
[58] Field of Search ........................................... 424/70.17

[56] References Cited

U.S. PATENT DOCUMENTS

| | | | |
|---|---|---|---|
| 4,948,579 | 8/1990 | Jacquet et al. | 424/70.17 |
| 5,147,635 | 9/1992 | Jachowicz et al. | 424/70.17 |
| 5,332,570 | 7/1994 | Bergstrom et al. | 424/72 |

FOREIGN PATENT DOCUMENTS

| | | |
|---|---|---|
| 0 235 783 | 9/1987 | European Pat. Off. . |
| 0 461 526 | 12/1991 | European Pat. Off. . |
| 2 472 382 | 12/1979 | France . |
| 2 495 931 | 12/1980 | France . |
| 2 707 486 | 1/1995 | France . |
| 54-86635 | 7/1979 | Japan . |
| 56-100710 | 8/1981 | Japan . |
| 62-205012 | 9/1987 | Japan . |
| 62-205013 | 9/1987 | Japan . |
| 62-205015 | 9/1987 | Japan . |
| 2-178216 | 7/1990 | Japan . |
| 2 066 310 | 7/1981 | United Kingdom . |
| WO 95/02391 | 1/1995 | WIPO . |

*Primary Examiner*—Peter F. Kulkosky
*Attorney, Agent, or Firm*—Finnegan, Henderson, Farabow, Garrett & Dunner, L.L.P.

[57] ABSTRACT

A cosmetic composition for the first stage of an operation for the permanent reshaping of keratinous material, in particular the hair, which consists in reducing the disulphide bonds of keratin, characterized in that it comprises at least one active agent suitable for the reduction of the disulphide bonds of keratin, at least one basifying agent chosen from ornithine, a salt of ornithine, lysine, a salt of lysine, arginine, and a salt of arginine, and at least one cationic polymer containing primary, secondary or tertiary amine groups or quaternary ammonium groups in the main chain.

A process for the treatment of keratinous material, in particular the hair, for the purpose of obtaining a permanent reshaping of the latter, in particular in the form of permanent-waved hair, the said process being characterized in that it includes the following steps: (i) a composition as defined above is applied to the keratinous material to be treated, the means (rollers) necessary for placing the keratinous material under mechanical tension being implemented before, during or after the said application, (ii) the keratinous material thus treated is then rinsed, (iii) an oxidizing composition is applied to the keratinous material thus rinsed, the treated keratinous material being separated from the means for placing under tension used in step (i) before or after the said application of the oxidizing composition, (iv) and, lastly, the keratinous material is rinsed again.

31 Claims, No Drawings

REDUCING COMPOSITION COMPRISING A BASIC AMINO ACID AND A CATIONIC POLYMER

The present invention relates to a novel cosmetic composition for the first stage of an operation for the permanent reshaping of keratinous material, in particular hair, comprising a basic amino acid as a basifying agent and cationic polymers.

The invention also relates to a process for treating keratinous material, in particular hair, for the purpose of obtaining a permanent reshaping of the latter, in particular in the form of permanent-waved hair.

It is known that the most common technique for obtaining a permanent reshaping of the hair consists, in a first stage, in opening the keratin —S—S— disulphide (cysteine) bonds using a composition containing a reducing agent (reduction step) followed, preferably after having rinsed the head of hair thus treated, by reconstituting, in a second stage, the said disulphide bonds by applying to the hair, which has been placed under tension beforehand (rollers and the like) an oxidizing composition (oxidation step, also known as the fixing step) so as to finally give to the hair the desired shape. This technique thus makes it equally possible either to make the hair wavy or to straighten it or to remove its curliness.

The new shape given to the hair by a chemical treatment such as above is remarkably long-lasting and in particular resists the action of washing with water or shampoos, as opposed to simple standard techniques for temporary reshaping, such as hairsetting.

The reducing compositions which may be used in order to carry out the first step of a permanent-waving operation generally contain, as reducing agents, sulphites, bisulphites, or, preferably, thiols. Among the thiols, those commonly used are cysteine and the various derivatives thereof, cysteamine and the derivatives thereof, thiolactic acid, thioglycolic acid and the esters thereof, in particular glyceryl monothioglycolate, and thioglycerol.

In this regard, and although it possesses an unpleasant odour, thioglycolic acid is particularly effective and thus constitutes the compound of reference in permanent-waving in order to reduce the disulphide bonds of keratin; as for cysteine, this product has a much fainter odour than that of thioglycolic acid or glyceryl monothioglycolate, but the degree of curliness obtained is, unfortunately, inferior and far from being entirely satisfactory.

Since these reducing agents have a deteriorating effect on the hair, it has been recommended to combine them with the cationic polymers.

However, these compositions have overall a strong and stinging odour, which inconveniences the user and those in the vicinity, more particularly in hair salons in which treatments of this type are used particularly frequently. The unpleasant odour of these compositions is due to the reducing agents and the basifying agents; the basifying agents generally used either being aqueous ammonia or monoethanolamine.

Furthermore, use of these compositions on sensitized hair in order to obtain a permanent reshaping of this hair is not entirely satisfactory, either as regards the result of the curliness or as regards the quality of the hair.

Another problem with the permanent-waving techniques known to date is that their repeated application on the hair induces a considerable modification in the behaviour of the hair over time, in particular as regards its subsequent ability to be correctly dyed.

Thus, it is first observed that, on hair which has undergone a few permanent-waving operations, the coloration will be much more pronounced than that obtained on the same hair but not permanent-waved; this thus poses a problem in all the cases in which the dyeing operation is performed on a head of hair which was originally permanent-waved but which, in the intervening time, has also regrown (poor unison between the original permanent-waved hair and the new growth of hair not permanent-waved).

It is moreover observed that the dyeing becomes very difficult, or even impossible, if the head of hair to be dyed has previously undergone several permanent-waving operations.

Moreover, when the basifying agent present in order to buffer the pH of the reducing composition is chosen from carbonate-based products such as, for example, carbon dioxide, ammonium or alkaline carbonates or bicarbonates or organic carbonates such as, in particular, guanidine carbonate, it turns out, unfortunately, that the repeated application of the hair shaping/permanent reshaping operations using these carbonate-based reducing compositions combined with oxidizing compositions based on aqueous hydrogen peroxide solution results in a gradual and marked impairment over time of the quality of the hair, in particular as regards the softness of the fibres, which tend to become increasingly coarse.

The aim of the present invention is, in particular, to solve the above problems.

More precisely, the aim of the present invention is to propose a composition such as above which makes it possible to limit, or even to prevent, the mechanical degradation of the hair after repetition of the treatment.

Another aim of the invention is to propose a composition such as the above which is, overall, largely odourless, on the one hand, and largely non-irritant to the skin and/or the scalp, on the other hand.

The aim of the invention is also to propose a novel cosmetic composition for the first stage of an operation for the permanent reshaping of the hair which makes it possible to obtain satisfactory results in terms of yield, liveliness and attractiveness of the curls.

Lastly, the aim of the present invention is to propose a cosmetic composition for the first stage of an operation for the permanent reshaping of the hair which makes it possible to improve the subsequent dyeing qualities.

Now, it has been found by the inventors that these aims, and others, could be achieved successfully by making a suitable selection of the compounds of the so-called reducing composition.

Thus, according to the present invention, a novel cosmetic composition is now proposed for the first stage of an operation for the permanent reshaping of keratinous material, in particular hair, which comprises reducing the disulphide bonds of keratin, this being known as the reducing composition, wherein the composition comprises at least one active agent suitable for the reduction of the disulphide bonds of keratin, at least one basifying agent chosen from ornithine, lysine, arginine, and the salts thereof, and at least one cationic polymer containing primary, secondary or tertiary amine groups or quaternary ammonium groups in the main chain.

The present invention also relates to a process for the treatment of keratinous material, in particular hair, for the purpose of obtaining a permanent reshaping of the latter, in particular in the form of permanent-waved hair, the said process being characterized in that it includes the following steps:

(i) a composition as defined above is applied to the keratinous material to be treated, the means (rollers) necessary for placing the keratinous material under mechanical tension being implemented before, during or after the said application, (ii) the keratinous material thus treated is then rinsed, (iii) an oxidizing composition is applied to the keratinous material thus rinsed, the treated keratinous material being separated from the means for placing under tension used in step (i) before or after the said application of the oxidizing composition, and lastly (iv) the keratinous material is rinsed again.

The process according to the invention is generally suitable for obtaining a permanent-waved head of hair.

When applied to a head of healthy hair, even repeatedly, the composition according to the invention has the main advantages, inter alia, of giving, without the release of unpleasant odours and in a non-irritant manner to the skin and/or the scalp, hair which is less damaged, mechanically strong, and which has beautiful curls.

However, other characteristics, aspects and advantages of the invention will appear even more clearly on reading the detailed description which follows, as well as the various concrete, but in no way limiting, examples intended to illustrate it.

Although the account which follows is essentially centered around the particular case of the treatment of the hair, it will be noted here that the process according to the invention may be applied to any keratinous material in general, in particular eyelashes, moustaches, body hairs, wool and the like.

Among the active agents which are suitable for the reduction of the disulphide bonds of keratin, mention may be made of sulphites, bisulphites, or, preferably, thiols. Among these thiols, those preferably used are cysteine and the derivatives thereof, cysteamine and the derivatives thereof, 3-mercaptopropionic acid, thiolactic acid, thioglycolic acid and the esters or salts thereof, in particular glyceryl monothioglycolate, and thioglycerol.

These active agents may be used alone or as a mixture.

Among the basifying agents used in the present invention, it is preferred to use arginine or a salt thereof.

The basifying agent chosen from ornithine, lysine, arginine, and salts thereof, is thus used in order to reach the desired pH, it being necessary for the pH to generally range from 5 to 11.5.

It is possible to use these basifying agents alone or as a mixture. They may also be present with other basifying agents, such as aqueous ammonia, monoethanolamine or carbonate-based products. These other basifying agents are preferably present in amounts which do not allow them to give the compositions containing them the above-mentioned drawbacks, such as the disagreeable odours.

In particular, these other basifying agents are used in order to neutralize the reducing agents of acidic nature.

When thioglycolic acid, thiolactic acid, 3-mercaptopropionic acid, cysteine or cysteamine, or one of the salts or derivatives thereof, is used as reducing agent, the pH of the entire composition according to the invention preferably ranges from 6.5 to 11.5, and even more preferably ranges from 7 to 10.

When the esters of thioglycolic acid or thiolactic acid or 3-mercaptopropionic acid are used as reducing agent, the pH of the entire composition according to the invention preferably ranges from 5 to 11, and even more preferably ranges from 6 to 9.5.

The cationic polymers used in the present invention contain primary, secondary or tertiary amine groups or quaternary ammonium groups in the main chain. They generally have a molecular weight of greater than 500, preferably of greater than 1000.

The cationic polymers preferably used in the present invention are chosen from:

(1) polymers comprising piperazinyl units and divalent alkylene or hydroxyalkylene radicals containing straight or branched chains, which are optionally interrupted by oxygen, sulphur or nitrogen atoms or by aromatic or heterocyclic rings, as well as the oxidation and/or quaternization products of these polymers. Such polymers are described in particular in French patents 2,162,025 and 2,280,361, which are specifically incorporated by reference herein;

(2) water-soluble polyamino amides prepared in particular by polycondensation of an acidic compound with a polyamine; these polyamino amides may be crosslinked with an epihalohydrin, a diepoxide, a dianhydride, an unsaturated dianhydride, a bis-unsaturated derivative, a bis-halohydrin, a bis-azetidinium, a bis-haloacyidiamine, a bis-alkyl halide or alternatively with an oligomer resulting from the reaction of a difunctional compound which is reactive towards a bis-halohydrin, a bis-azetidinium, a bis-haloacyidiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides may be alkylated or, if they contain one or more tertiary amine functions, they may be quaternized.

Such polymers are described in particular in French patents 2,252,840 and 2,368,508, which are specifically incorporated herein by reference. (3) polyamino amide derivatives resulting from the condensation of polyalkylene polyamines with polycarboxylic acids followed by an alkylation with difunctional agents. Mention may be made, for example, of adipic acid-dialkylaminohydroxyalkyl-dialkylenetriamine polymers in which the alkyl radical contains from 1 to 4 carbon atoms and preferably denotes methyl, ethyl or propyl.

Such polymers are described in particular in French patent 1,583,363, which is specifically incorporated herein by reference.

Among these derivatives, mention may be made more particularly of the adipic acid/dimethylaminohydroxypropyl/diethylenetriamine polymers sold under the name "Cartaretine F, F4 or F8" by the company Sandoz. (4) polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid ranges from 0.8:1 to 1.4:1; the polyamino amide resulting therefrom being reacted with epichlorohydrin in a molar ratio of epichlorohydrin relative to the secondary amine group of the polyamino amide ranging from 0.5:1 to 1.8:1.

Such polymers are described in particular in U.S. Pat. Nos. 3,227,615 and 2,961,347, which are specifically incorporated herein by reference.

Polymers of this type are marketed in particular under the name "Hercosett 57" by the company Hercules Inc. or alternatively under the name "PD 1/0" or "Delsefte 101" by the company Hercules in the case of the adipic acid/epoxypropyl/diethylenetriamine copolymer.

(5) cyclohomopolymers of methyldiallylamine or of dimethyldiallylammonium such as homopolymers containing, as main chain constituents, units corresponding to the formulae (I) or (II)

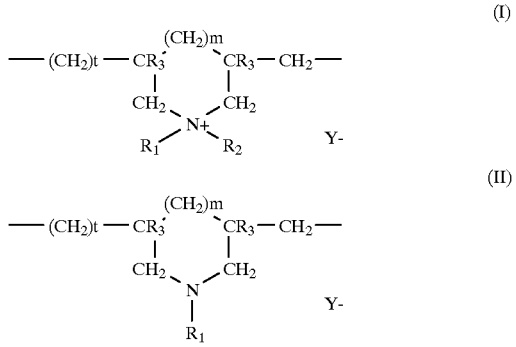

in which formulae m and t are equal to 0 or 1, the sum m+t being equal to 1;

R3 denotes a hydrogen atom or a methyl radical;

R1 and R2, independently of each other, denote an alkyl group having from 1 to 22 carbon atoms, a hydroxyalkyl group in which the alkyl group preferably has 1 to 5 carbon atoms, a lower amidoalkyl group, or R1 and R2 may denote, together with the nitrogen atom to which they are attached, heterocyclic groups such as piperidyl or morpholinyl; and Y' is an anion such as bromide, chloride, acetate, borate, citrate, tartrate, bisulphate, bisulphite, sulphate or phosphate.

Among the polymers defined above, mention may be made more particularly of the homopolymer of dimethyldiallylammonium chloride sold under the name "Merquat 100" by the company Merck.

These polymers are described in particular in French patent 2,080,759 and in its Certificate of Addition 2,190,406, both of which are specifically incorporated by reference herein.

(6) the quaternary diammonium polymer containing repeating units corresponding to the formula:

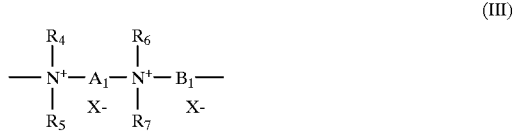

in which

R4, R5, R6 and R7, which may be identical or different, represent aliphatic, alicyclic or arylaliphatic radicals containing from 1 to 20 carbon atoms or lower hydroxyalkylaliphatic radicals, or alternatively R4, R5, R6 and R7, together or separately, constitute, with the nitrogen atoms to which they are attached, heterocycles optionally containing a second hetero atom other than nitrogen or alternatively R4, R5, R6 and R7 represent a linear or branched C1–C6 alkyl radical substituted with a nitrile, ester, acyl, amide or —CO—O—R8—D or —CO—NH—R8—D radical where R8 is an alkylene and D is a quaternary ammonium group;

A1 and B1 represent polymethylene groups containing from 2 to 20 carbon atoms which may be linear or branched, saturated or unsaturated and which may contain, bonded to or intercalating in the main chain, one or more aromatic rings or one or more oxygen or sulphur atoms or sulphoxide, sulphone, disulphide, amino, alkylamino, hydroxyl, quaternary ammonium, ureido, amide or ester groups;

X⁻ denotes an anion derived from an inorganic or organic acid;

A1, R4 and R6 may form, together with the two nitrogen atoms to which they are attached, a piperazinyl ring;

in addition, if A1 denotes a linear or branched, saturated or unsaturated alkylene or hydroxyalkylene radical, B1 may also denote a group (CH2)n—CO—D—OC—(CH2)n— in which D denotes:

a) a glycol residue of formula: O—Z—O—, where Z denotes a linear or branched hydrocarbon radical or a group corresponding to one of the following formulae:

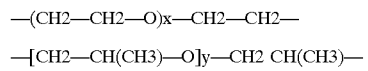

—[CH2—CH(CH3)—O]y—CH2 CH(CH3)— where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon radical, or alternatively the divalent radical —CH2—CH2—S—S—CH2—CH2—; or d) a ureylene group of formula: —NH—CO—NH—.

X⁻ is preferably an anion such as chloride or bromide.

These polymers generally have a molecular mass ranging from 1000 to 100,000.

Polymers of this type are described in particular in French patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 1,001,432, 3,929,990, 3,966,904, 4,005,193, 4,025,617, 4,025,627, 4,025,653, 1,026,945 and 4,027,020, all of which are specifically incorporated by reference herein.

(7) quaternary polyammonium polymers comprising units of formula (IV):

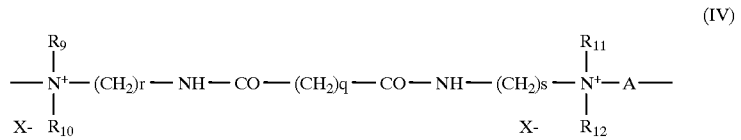

in which

R9, R10, R11 and R12, which may be identical or different, represent a hydrogen atom or a methyl, ethyl, propyl, β-hydroxyethyl, β-hydroxypropyl or —CH2CH2(OCH2CH2)pOH radical;

where p is equal to 0 or to an integer from 1 to 6, with the proviso that R9, R10, R11 and R12 do not simultaneously represent a hydrogen atom;

r and s, which may be identical or different, are integers from 1 to 6;

q is equal to 0 or to an integer from 1 to 34;

X denotes a halogen atom; and

A denotes a dihalide radical or, preferably, represents —CH2—CH2—O—CH2—CH2—.

Such compounds are described in particular in patent application EP-A-122,324, which is incorporated by reference herein.

Among those which may be mentioned, for example, are the products "Mirapol A 15", "Mirapol AD1", "Mirapol AZ1" and "Mirapol 175" sold by the company Miranol.

Among these cationic polymers, it is preferred to use the polymers chosen from Merquat 100 and the compound of formula (III) in which R4, R5, R6 and R7 represent a methyl radical, A1 represents a radical of formula —(CH2)3— and B1 represents a radical of formula —(CH2)6— and X$^-$ represents a chloride anion (referred to hereinafter as Mexomer PO).

According to a preferred embodiment, the reducing composition also contains a surfactant of nonionic, anionic, cationic or amphoteric type commonly used in permanent-waving reducing compositions and, among these surfactants, mention may be made of alkyl sulphates, alkyl benzenesulphates, alkyl ether sulphates, alkyl sulphonates, quaternary ammonium salts, alkylbetaines, oxyethylenated alkylphenols, fatty acid alkanolamides, oxyethylenated fatty acid esters and other nonionic surfactants of the hydroxypropyl ether type.

When the reducing composition contains at least one surfactant, this surfactant is generally present at a maximum concentration of 30% by weight, but preferably ranging from 0.5 to 10% by weight, relative to the total weight of the reducing composition.

With the aim of improving the cosmetic properties of the hair or alternatively of attenuating or avoiding its degradation, the reducing composition may also contain a treating agent of anionic, nonionic or amphoteric nature.

Treating agents which may be used are linear or cyclic volatile or non-volatile silicones and mixtures thereof, polydimethylsiloxanes, quaternized polyorganosiloxanes such as those described in French patent application No. 2,535,730, which is specifically incorporated herein by reference, polyorganosiloxanes containing aminoalkyl groups modified with alkoxycarbonylalkyl groups, such as those described in U.S. Pat. No. 4,749,732, which is specifically incorporated herein by reference, polyorganosiloxanes such as the polydimethylsiloxane-polyoxyalkyl copolymer of the dimethicone copolyol type, a polydimethylsiloxane containing stearoxy end-groups (stearoxydimethicone), a polydimethylsiloxane-dialkylammonium acetate copolymer or a polydimethylsiloxane polyalkylbetaine copolymer which are described in British patent application No. 2,197,352, which is specifically incorporated herein by reference, polysiloxanes organically modified with mercapto or mercaptoalkyl groups, such as those described in French patent No. 1,530,369, which is specifically incorporated herein by reference, and in European patent application No. 295,780, which is specifically incorporated herein by reference, as well as silanes such as stearoxytrimethylsilane.

The reducing composition may also contain other treating ingredients such as waxes, swelling agents, penetration agents or agents which allow the effectiveness of the reducing agent to be reinforced, such as dimethylisosorbitol, urea and derivatives thereof, pyrrolidone, N-alkylpyrrolidones, thiamorpholinone, alkyl ethers of alkylene glycol or of dialkylene glycol such as, for example, propylene glycol monomethyl ether, dipropylene glycol monomethyl ether, ethylene glycol monoethyl ether and diethylene glycol monoethyl ether, $C_3$–$C_6$ alkanediols such as, for example, 1,2-propanediol and 1,2-butanediol, 2-imidazolidinone and other compounds such as fatty alcohols, lanolin derivatives, active ingredients such as pantothenic acid, agents for preventing hair loss, antidandruff agents, thickeners, suspension agents, sequestering agents, opacifiers, dyes and sunscreens, as well as fragrances and preserving agents.

Lastly, the compositions may also be in so-called "self-neutralizing" or alternatively "self-regulating" form and, in this case, the reducing agents are combined with at least one disulphide known for its use in a self-neutralizing permanent-waving reducing composition.

Among such known disulphides which may be mentioned in particular are dithiodiglycolic acid, dithioglycerol, cystamine, N,N'-diacetylcystamine, cystine, pantethine and the disulphides of the N-(mercaptoalkyl)-ω-hydroxyalkylamides described in patent application EP-A-354,835, which is specifically incorporated herein by reference, the disulphides of the 4-N-mono or 4-N,N-dialkylmercaptobutyramides described in patent application EP-A-368,763, which is specifically incorporated herein by reference, the disulphides of the aminomercaptoalkylamides described in patent application EP-A-432,000, which is specifically incorporated herein by reference, the disulphides of the derivatives of the N-(mercaptoalkyl) succinamic acids or of the N-(mercaptoalkyl)succinimides described in patent application EP-A-465,342, which is specifically incorporated herein by reference, and the disulphides of the alkylaminomercaptoalkylamides described in patent application EP-A-514,282, which is specifically incorporated herein by reference. These disulphides are generally present in a molar ratio of 0.5 to 2.5 and preferably of 1 to 2 relative to the reducing agent (see U.S. Pat. No. 3,768,490, which is specifically incorporated herein by reference).

In the permanent-waving reducing compositions which may be used within the context of the invention, the reducing agents mentioned above are generally present at a concentration which may range from 1 to 20% by weight and preferably ranges from 5 to 15% by weight relative to the total weight of the reducing composition.

In the permanent-waving reducing compositions which may be used within the context of the invention, the cationic polymers containing primary, secondary or tertiary amine groups or quaternary ammonium groups in the main chain as defined above are generally present at a concentration ranging from 0.1 to 5% by weight and preferably ranging from 0.5 to 3% by weight relative to the total weight of the reducing composition.

In the permanent-waving reducing compositions which may be used within the context of the invention, the basifying agent as defined above is present at a concentration sufficient to adjust the pH of this composition, this concentration generally ranging from 0.01 to 20% by weight and preferably ranging from 0.1 to 18% by weight relative to the total weight of the reducing composition.

The reducing composition may be in the form of a lotion, which may or may not be thickened, a cream, a gel or any other suitable form.

According to one variant of the invention, the reducing composition according to the invention is packaged such that it jointly contains the compounds described above, i.e., the composition according to the invention is contained in a device containing a single compartment.

According to another variant of the invention, the reducing composition according to the invention is contained in a device containing at least two compartments, the constituents of the reducing composition being mixed together at the time of use. Thus, more particularly, at least one active agent which is suitable for the reduction of the disulphide bonds of keratin is found in a first compartment, and at least one basifying agent chosen from ornithine, lysine, arginine, and salts thereof, and optionally, suitable fragrances, are found in the second compartment. The other compounds, and more particularly the cationic polymer containing primary, secondary or tertiary amine groups or quaternary ammonium groups in the main chain, are found either in one of these two compartments, preferably in the second compartment, or in other compartments. This variant of the invention makes it possible to provide a reducing composition according to the invention which has very little odour.

The reducing composition may also be of the exothermic type, that is to say of the type giving rise to a certain amount of heating up when applied to the hair, this providing a pleasant sensation to the person on whom the permanent-waving or hair straightening operation is being carried out.

The reducing composition may also contain a solvent such as, for example, ethanol, propanol, isopropanol, propyleneglycol or glycerol at a maximum concentration of 20% relative to the total weight of the composition.

The vehicle for the compositions is preferably water or an aqueous-alcoholic solution of a lower alcohol such as ethanol, isopropanol or butanol.

When the compositions are intended for an operation to straighten or remove the curliness from the hair, the reducing composition is preferably in the form of a thickened cream so as to keep the hair as straight as possible. These creams are produced, in the form of "heavy" emulsions, based for example on glyceryl stearate, on glycol stearate, on self-emulsifiable waxes, on fatty alcohols, etc.

It is also possible to use liquids or gels containing thickeners such as carboxyvinyl polymers or copolymers which "stick" the hair together and keep it in a smooth position during the time for which the hair is exposed to the composition.

In accordance with the first step of the process according to the present invention (step (i)), the composition according to the invention is thus applied to the hair to be treated, which hair has preferably been made wet beforehand.

This application may be performed, before, during or after the usual step of placing the hair under tension in a shape corresponding to the desired final shape of the hair (curls for example), it being possible for this step itself to be carried out by any suitable means, in particular mechanical means, known per se for keeping hair under tension such as, for example, rollers, curlers and the like.

This application comprises an exposure time, to allow the composition according to the invention to act, which generally ranges from 5 to 60 minutes, preferably ranging from 5 to 30 minutes.

In a second step of the process according to the invention (step (ii)), the hair impregnated with reducing composition is then rinsed carefully, generally with water.

According to a third step of the treatment process according to the invention (step (iii)), an oxidizing composition which allows the disulphide bonds of keratin to reform (fixing step) is applied to the hair thus rinsed.

The oxidizing composition is of the type commonly used and contains as oxidizing agent, for example, aqueous hydrogen peroxide solution, an alkaline bromate, a persalt or a mixture of alkaline bromate and a persalt.

The concentration of aqueous hydrogen peroxide solution may range from 1 to 10 volumes but is preferably 8 volumes, the concentration of alkaline bromate is from 1 to 12% and that of persalt is from 0.1 to 15% by weight relative to the total weight of the oxidizing composition.

The pH of the oxidizing composition may range from 2 to 8, but preferably from 3 to 6.

The aqueous hydrogen peroxide solution may be stabilized, for example, with phenacetin, acetanilide, mono- and trisodium phosphates or with 8-hydroxyquinoline sulphate.

The oxidizing composition may also contain basifying or acidifying agents, preserving agents, sequestering agents, opacifiers and optionally a cationic polymer as defined above for the reducing composition.

The mechanical means (rollers, curlers and the like) which held the hair in the desired shape throughout the treatment may be removed from the head of hair before or after the fixing step.

Lastly, in the final step of the process according to the invention (step (iv)), the hair thus treated is rinsed thoroughly.

Another subject of the present invention is a process for straightening or removing the curliness from the hair, in which a reducing composition according to the invention is applied to the hair and the hair is then subjected to a mechanical reshaping which allows it to be fixed in its new shape, by an operation of smoothing out the hair with the back or the teeth of a comb or by hand. During the general exposure time of 5 to 60 minutes, in particular of 5 to 30 minutes, the hair is again smoothed out one or more times and is then rinsed thoroughly, and an oxidizing or fixing composition as defined above is applied, which is left to act for about 2 to 10 minutes, then the hair is rinsed thoroughly.

Concrete examples illustrating the invention will now be given. Such examples in no way limit the invention. In these examples, AM means active material.

EXAMPLE 1

A reducing composition for the permanent reshaping of the hair is prepared according to the invention by mixing together the following ingredients:

| | |
|---|---|
| -thioglycolic acid | 9.2 g |
| -arginine | 2.0 g |
| -aqueous ammonia containing 20% NH3 | 9.3 g |
| | (1.86 g AM) |
| -mexomer PO | 1.0 g AM |
| -ammonium carbonate | 4.5 g |
| -cocoylamidopropylbetaine/glyceryl | 1.3 g |
| monolaurate (25/5) as a 30% aqueous solution | (0.39 g AM) |
| -fragrance | 0.4 g |
| -peptizing agent | 0.8 g |
| -sequestering agent | 0.4 g |
| -demineralized water | qs 100 g |
| | pH 8.3 |

This composition is applied to wet hair wound beforehand on hairsetting rollers. After the composition has been left to act for about 15 minutes, the hair is rinsed thoroughly with water and the following oxidizing composition is then applied:

| -aqueous hydrogen peroxide solution | qs 8 volumes pH3 |

The oxidizing composition is left to act for about 5 minutes, then the head of hair is rinsed thoroughly with water and the rollers are removed.

After drying under a hood, the hair has beautiful curls.

EXAMPLE 2

A reducing composition for the permanent reshaping of the hair is prepared according to the invention by mixing together the following ingredients:

| | |
|---|---|
| -thioglycolic acid | 6.2 g |
| -ammonium thioglycolate | 2.9 g |
| -arginine | 15.0 g |
| -mexomer PO | 1.0 g AM |
| -cocoylamidopropylbetaine/glyceryl monolaurate (25/5) as a 30% aqueous solution | 1.3 g (0.39 g AM) |
| -fragrance | 0.5 g |
| -peptizing agent | 1 g |
| -sequestering agent | 0.4 g |
| -demineralized water | qs 100 g pH 8.3 |

This composition is applied to wet hair wound beforehand on hairsetting rollers. After the composition has been left to act for about 15 minutes, the hair is rinsed thoroughly with water and the following oxidizing composition is then applied:

| -aqueous hydrogen peroxide solution | qs 8 volumes pH3 |

The oxidizing composition is left to act for about 5 minutes, then the head of hair is rinsed thoroughly with water and the rollers are removed.

After drying under a hood, the hair has beautiful curls.

EXAMPLE 3

The same composition as in Example 2 is prepared, but packaged in a two-compartment device.

| | |
|---|---|
| Compartment A: | |
| -thioglycolic acid | 6.2 g |
| -ammonium thioglycolate | 2.9 g |
| -sequestering agent | 0.4 g |
| -demineralized water | qs 30 g |
| Compartment B: | |
| -arginine | 15 g |
| -mexomer PO | 1.0 g AM |
| -cocoylamidopropylbetaine/glyceryl monolaurate (25/5) as a 30% aqueous solution | 1.3 g (0.39 g AM) |
| -fragrance | 0.5 g |
| -peptizing agent | 1 g |
| -demineralized water | qs 70 g |

By virtue of a better conservation of the fragrance (not in the presence of the thiols), this type of formulation makes it possible to afford a markedly improved odour.

Once the constituents of this composition have been mixed together, this composition is applied to wet hair wound beforehand on hairsetting rollers. After the composition has been left to act for about 15 minutes, the hair is rinsed thoroughly with water and the following oxidizing composition is then applied:

| -aqueous hydrogen peroxide solution | qs 8 volumes pH3 |

The oxidizing composition is left to act for about 5 minutes, then the head of hair is rinsed thoroughly with water and the rollers are removed.

After drying under a hood, the hair has beautiful curls.

EXAMPLE 4

The following four permanent reshaping reducing compositions were made:

| | |
|---|---|
| Reducing composition 1 (invention) | |
| -thioglycolic acid | 9.2 g |
| -sequestering agent | 0.4 g |
| -arginine | 1 g |
| -mexomer PO | 1 g AM |
| -water | qs 100 g |
| Reducing composition 2 (invention) | |
| -thioglycolic acid | 9.2 g |
| -sequestering agent | 0.4 g |
| -arginine | 1 g |
| -mexomer PO | 2 g AM |
| -water | qs 100 g |
| Reducing composition 3 (comparative) | |
| -thioglycolic acid | 9.2 g |
| -sequestering agent | 0.4 g |
| -arginine | 1 g |
| -hydrolysate of N-hydroxypropylcocoyldimethyl-ammonium collagen as a 30% aqueous solution | 1 g AM |
| -water | qs 100 g |
| Reducing composition 4 (comparative) | |
| -thioglycolic acid | 9.2 g |
| -sequestering agent | 0.4 g |
| -arginine | 1 g |
| -hydrolysate of quaternized wool keratin (MW 1350) as a 30% aqueous solution | 1 g AM |
| -water | qs 100 g |

Each reducing composition was applied to four locks of mildly sensitized hair. After the composition has been left to act for about 15 minutes, the locks are rinsed thoroughly with water and the following oxidizing composition is then applied:

| -aqueous hydrogen peroxide solution | qs 8 volumes pH3 |

The oxidizing composition is left to act for about 5 minutes and the locks are then rinsed thoroughly with water.

The locks of hair were then subjected to an oxidation dyeing process.

Lastly, the locks of hair were again subjected to a permanent reshaping process identical to that described above.

The locks of hair thus treated were then subjected to the following alkaline solubility test: the hair was immersed in a sodium hydroxide solution of concentration 0.1 mol/l for a period of 30 minutes and at a temperature of 60° C. The amount of hair remaining was then weighed. The amount of solubilized hair is thus determined. This measurement makes it possible to evaluate the degree of damage of the hair. The more the hair is degraded, the more it solubilizes.

The results, expressed as a percentage of solubilized hair (SA) and given for each reducing composition as the average of the results obtained on the four locks, are presented in the table below:

TABLE

| Composition | SA |
|---|---|
| Reducing composition 1 (invention) | 35.1% |
| Reducing composition 2 (invention) | 32.2% |
| Reducing composition 3 (comparative) | 49.6% |
| Reducing composition 4 (comparative) | 53.6% |

These results clearly show that in order to limit the mechanical degradation of hair subjected to various treatments, in particular to permanent reshaping treatments, the reducing compositions according to the invention, namely comprising a cationic polymer containing primary, secondary or tertiary amine groups or quaternary ammonium groups in the main chain, are more effective than reducing compositions comprising cationic polymers not containing any such groups in the main chain, such as quaternized protein hydrolysates.

We claim:

1. A cosmetic composition for the first stage of an operation for the permanent reshaping of keratinous material, whereby the disulphide bonds of keratin are reduced, wherein said composition comprises from 1 to 20% by weight, relative to the total weight of said composition, of at least one active agent suitable for the reduction of the disulphide bonds of keratin, from 0.01 to 20% by weight, relative to the total weight of said composition, of at least one basifying agent which is ornithine, a salt of ornithine, lysine, a salt of lysine, arginine or a salt of arginine, and from 0.1 to 5% by weight, relative to the total weight of said composition, of at least one cationic polymer containing primary, secondary or tertiary amine groups or quaternary ammonium groups in the main chain of said polymer, wherein said at least one cationic polymer is selected from:
   (a) polymers comprising piperazinyl units and divalent alkylene or hydroxyalkylene radicals containing straight or branched chains, which are optionally interrupted by oxygen, sulphur or nitrogen atoms or by aromatic or heterocyclic rings, and the oxidation and/or quaternization products of said polymers (a);
   (b) water-soluble polyamino amides which are optionally crosslinked and/or alkylated;
   (c) polyamino amide derivatives resulting form the condensation of polyalkylene polyamines with polycarboxylic acids followed by an alkylation with difunctional agents;
   (d) polymers obtained by reaction of a polyalkylene polyamine containing two primary amine groups and at least one secondary amine group with a dicarboxylic acid;
   (e) cyclohomopolymers of methyldiallylamine or of dimethyldiallylammonium;
   (f) quaternary diammonium polymers; and
   (g) quaternary polyammonium polymers other than those recited in (f).

2. A composition according to claim 1 wherein said keratinous material is hair.

3. A composition according to claim 1 wherein said active agent is selected from sulphites, bisulphites, thiols, and mixtures thereof.

4. A composition according to claim 3 wherein said thiols are selected from cysteine and derivatives thereof, cysteamine and derivatives thereof, 3-mercaptopropionic acid, thiolactic acid, thioglycolic acid, and esters and salts of any of said thiol compounds.

5. A composition according to claim 3 wherein said active agent is selected from thiols.

6. A composition according to claim 1 wherein the basifying agent is arginine or a salt thereof.

7. A composition according to claim 1 wherein the composition further comprises at least one additional basifying agent selected from aqueous ammonia, monoethanolamine and carbonate-based basifying agents.

8. A composition according to claim 7 wherein said reducing agent is of an acidic nature and further wherein said at least one additional basifying agent is present in an amount sufficient to neutralize said reducing agent of an acidic nature.

9. A composition according to claim 8 wherein said at least one polymer is a homopolymer comprising, as main chain constituents, units corresponding to the formulae (I) or (II):

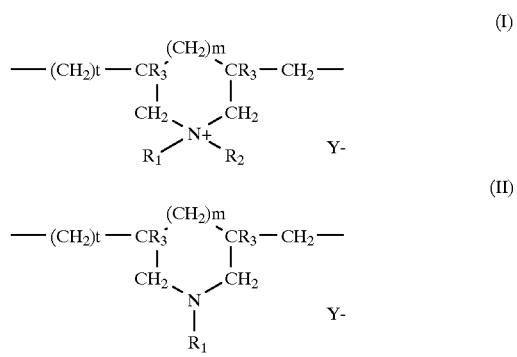

in which formulae m and t are equal to 0 or 1, the sum m+t being equal to 1;

R3 denotes a hydrogen atom or a methyl radical;

R1 and R2, independently of each other, denote an alkyl group having from 1 to 22 carbon atoms, a hydroxyalkyl group, a lower amidoalkyl group or R1 and R2 may denote, together with the nitrogen atom to which they are attached, heterocyclic groups; and Y' is an anion.

10. A composition according to claim 9, wherein in said hydroxyalkyl group, the alkyl group has 1 to 5 carbon atoms.

11. A composition according to claim 9, wherein said anion is bromide, chloride, acetate, borate, citrate, tartrate, bisulphate, bisulphite, sulphate or phosphate.

12. A composition according to claim 9, wherein said heterocyclic groups are selected from piperidyl and morpholinyl.

13. A composition according to claim 9 wherein said at least one polymer is Merquat 100 and further wherein said quaternary diammonium polymers contain repeating units corresponding to the formula (III):

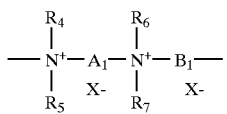

in which R4, R5, R6 and R7 represent a methyl radical, A1 represents a radical of formula —(CH2)3— and B1 represents a radical of formula —(CH2)6—and X⁻ represents a chloride anion.

14. A composition according to claim 1 further comprising a surfactant of nonionic, anionic, cationic or amphoteric type.

15. A composition according to claim 1 wherein the active agent suitable for the reduction of the disulphide bonds of keratin is combined with at least one disulphide.

16. A composition according to claim 1 wherein the active agent suitable for the reduction of the disulphide bonds of keratin is present at a concentration ranging from 5 to 15% by weight relative to the total weight of the said composition.

17. A composition according to claim 1 wherein said cationic polymer containing primary, secondary or tertiary amine groups or quaternary ammonium groups in the main chain is present at a concentration ranging from 0.5 to 3% by weight relative to the total weight of the said composition.

18. A composition according to claim 1 wherein said basifying agent is present at a concentration ranging from 0.1 to 18% by weight relative to the total weight of the reducing composition.

19. A composition according to claim 1 wherein said composition is in the form of a lotion, which may or may not be thickened, a cream or a gel.

20. A packaging device comprising, in one or more compartments, a composition according claim 1.

21. A device according to claim 20 wherein said device contains:
   at least two compartments; wherein
   said at least one active agent which is suitable for the reduction of the disulphide bonds of keratin is contained in a first compartment; and
   said at least one basifying agent and optionally fragrances are contained in a second compartment.

22. A process for the treatment of keratinous material to obtain a permanent reshaping of said keratinous material comprising the steps of:
   (i) applying a composition according to claim 1 to said keratinous material, wherein means necessary for placing said keratinous material under mechanical tension are implemented before, during or after said application of said composition;
   (ii) rinsing said keratinous material after step (i) and before step (iii);
   (iii) after step (ii) and before step (iv), applying an oxidizing composition to said keratinous material, said keratinous material being separated from said means for placing under tension used in step (i) before or after said application of the oxidizing composition; and
   (iv) lastly, rinsing said keratinous material.

23. A process according to claim 22, wherein said keratinous material is hair, wherein said means for placing said keratinous material under mechanical tension is rollers, and wherein said permanent reshaping is in the form of a permanent wave.

24. A process according to claim 22 wherein said keratinous material is hair and wherein as a result of steps (i) to (iv), said hair is permanently waved.

25. A process according to claim 22 wherein said rinsing step (ii) is carried out from 5 to 60 minutes after applying said composition in step (i).

26. A process according to claim 25 wherein said rinsing step (ii) is carried out from 5 to 30 minutes after applying said composition in step (i).

27. A process for straightening or removing the curliness from hair, comprising the steps of:
   (i) applying a composition according to claim 1 to hair;
   (ii) after step (i) and before step (iii), subjecting said hair one or more times to a mechanical reshaping, whereby said hair is fixed in a new shape;
   (iii) thoroughly rinsing, after step (ii) and before step (iv), said hair;
   (iv) applying to said hair, after step (iii) and before step (v), an oxidizing composition; and
   (v) lastly, rinsing said hair thoroughly.

28. A process according to claim 27 wherein said rinsing step (iii) is carried out from 5 to 60 minutes after applying said composition in step (i).

29. A process according to claim 28 wherein said rinsing step (iii) is carried out from 5 to 30 minutes after applying said composition in step (i).

30. A process according to claim 27 wherein said rinsing step (v) is carried out from 2 to 10 minutes after applying said composition in step (iv).

31. A process according to claim 27 wherein said mechanical reshaping is effected by the back of a comb, by the teeth of a comb, or by hand.

* * * * *